United States Patent
Fetterly et al.

(10) Patent No.: US 11,058,392 B2
(45) Date of Patent: Jul. 13, 2021

(54) SYSTEM AND METHOD FOR CORRECTING BIAS IN MEASUREMENTS IN AN IMAGING SYSTEM FROM NON-STATIONARY NOISE IN CHANNELIZED HOTELLING OBSERVERS

(71) Applicant: Mayo Foundation for Medical Education and Research, Rochester, MN (US)

(72) Inventors: Kenneth A. Fetterly, Spring Valley, MN (US); Christopher P. Favazza, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 27 days.

(21) Appl. No.: 16/471,526

(22) PCT Filed: Dec. 19, 2017

(86) PCT No.: PCT/US2017/067194
§ 371 (c)(1),
(2) Date: Jun. 19, 2019

(87) PCT Pub. No.: WO2018/118844
PCT Pub. Date: Jun. 28, 2018

(65) Prior Publication Data
US 2019/0320996 A1      Oct. 24, 2019

Related U.S. Application Data

(60) Provisional application No. 62/436,707, filed on Dec. 20, 2016.

(51) Int. Cl.
*A61B 6/00* (2006.01)

(52) U.S. Cl.
CPC ............ *A61B 6/585* (2013.01); *A61B 6/52* (2013.01); *A61B 6/5205* (2013.01);
(Continued)

(58) Field of Classification Search
CPC ......... A61B 6/504; A61B 6/52; A61B 6/5205; A61B 6/5211; A61B 6/5258;
(Continued)

(56) References Cited

U.S. PATENT DOCUMENTS 6,272,200 B1 * 8/2001 Pan ...................... G06T 11/005
378/15
7,289,654 B2 * 10/2007 Muller ................... A61B 6/583
378/207

(Continued)

OTHER PUBLICATIONS

Robert M. Gagne et al., Toward objective and quantitative evaluation of imaging systems using images of phantoms, Med. Phys. 33 (1), Jan. 2006.*

(Continued)

*Primary Examiner* — Allen C. Ho
(74) *Attorney, Agent, or Firm* — Quarles & Brady LLP

(57) ABSTRACT

Systems and methods for correcting images acquired with an imaging system for measurement bias from non-stationary noise in model observers are described. A biased detectability index is estimated from signal present and signal absent condition images and an estimate of the bias from non-stationary noise is also estimated. This bias is then removed from the detectability index to provide an assessment of detectability of the imaging system.

13 Claims, 5 Drawing Sheets

(52) U.S. Cl.
CPC .......... *A61B 6/5211* (2013.01); *A61B 6/5258* (2013.01); *A61B 6/5294* (2013.01); *A61B 6/54* (2013.01); *A61B 6/542* (2013.01); *A61B 6/545* (2013.01); *A61B 6/58* (2013.01); *A61B 6/582* (2013.01); *A61B 6/583* (2013.01)

(58) Field of Classification Search
CPC ......... A61B 6/5294; A61B 6/54; A61B 6/542; A61B 6/545; A61B 6/58; A61B 6/582; A61B 6/583; A61B 6/585; A61B 6/586
USPC .......................................... 378/62, 204, 207
See application file for complete search history.

(56) References Cited

U.S. PATENT DOCUMENTS

| | | | |
|---|---|---|---|
| 7,480,365 B1* | 1/2009 | Topfer | A61B 6/032 378/108 |
| 8,698,087 B2* | 4/2014 | Surti | G01T 1/00 250/363.04 |
| 8,885,906 B2* | 11/2014 | Weitzel | A61B 6/583 382/131 |
| 8,891,849 B2* | 11/2014 | Rohler | A61B 6/032 382/132 |
| 9,230,354 B2* | 1/2016 | O'Connor | A61B 6/4258 |
| 9,681,851 B2* | 6/2017 | Rohler | A61B 6/542 |
| 9,848,847 B2* | 12/2017 | Boedeker | A61B 6/544 |
| 9,936,924 B2* | 4/2018 | Stayman | A61B 6/547 |
| 9,947,117 B2* | 4/2018 | Raupach | G06T 11/005 |
| 10,022,098 B2* | 7/2018 | Kleinszig | A61B 6/032 |
| 10,064,591 B2* | 9/2018 | Wang | A61B 6/542 |
| 10,595,805 B2* | 3/2020 | Mainprize | G16H 30/40 |
| 10,732,309 B2* | 8/2020 | McCollough | G01T 1/2985 |
| 2016/0296196 A1 | 10/2016 | Boedeker et al. | |

OTHER PUBLICATIONS

Brandon Gallas, Variance of the channelized-hotelling observer from a finite number of trainers and testers, Proceedings of SPIE, vol. 5034, Medical Imaging 2003: Image Perception, Observer Performance, and Technology Assessment, May 22, 2003.*

Heang-Ping Chan et al., Classifier design for computer-aided diagnosis: Effects of finite sample size on the mean performance of classical and neural network classifiers, Med. Phys. 26 (12), Dec. 1999.*

Keinosuke Fukunaga and Raymond R. Hayes, IEEE Transactions on Pattern Analysis and Machine Intelligence, vol. 11, No. 8, Aug. 1989.*

International Search Report from Parent PCT/US17/67194, dated Mar. 6, 2018.

Fetterly, et al., Direct estimation and correction of bias from temporally variable non-stationary noise in a channelized Hotelling model observer, Phys. Med. Biol. 61, 5606-5620, Jul. 6, 2016.

Siewerdsen, et al., Optimization of x-ray imaging geometry (with specific application to flat-panel cone-beam computed tomography), Medical Physics, vol. 27, No. 8, Aug. 2000.

Abbey, et al., Observer efficiency in discrimination tasks simulating malignant and benign breast lesions imaged with ultrasound, IEEE Trans Med Imaging. Feb. 2006; 25(2): 198-209.

* cited by examiner

SYSTEM AND METHOD FOR CORRECTING BIAS IN MEASUREMENTS IN AN IMAGING SYSTEM FROM NON-STATIONARY NOISE IN CHANNELIZED HOTELLING OBSERVERS

CROSS-REFERENCE TO RELATED APPLICATIONS

This application is a 371 U.S. National Phase Entry of PCT/US2017/067194, filed Dec. 19, 2017, which claims the benefit of U.S. Provisional Patent Application Ser. No. 62/436,707, filed on Dec. 20, 2016, and entitled "SYSTEM AND METHOD FOR CORRECTING IMAGING SYSTEM MEASUREMENT BIAS FROM NON-STATIONARY NOISE IN MODEL OBSERVERS," each of which is herein incorporated by reference in its entirety.

BACKGROUND

Channelized hoteling observer ("CHO") has been previously implemented to assess performance of x-ray angiography systems. Subsequent applications of the model over a range of detector target dose ("DTD") demonstrated measurement bias for experimental conditions, which resulted in relatively low estimates of detectability index, in particular for small objects and low DTD. Thus, there remains a need for systems and methods for estimating and correcting non-stationary noise bias to facilitate accurate detectability index estimates.

SUMMARY OF THE DISCLOSURE

The present disclosure addresses the aforementioned drawbacks by providing a method for generating an unbiased detectability index from images acquired with an imaging system. A signal present image acquired with an imaging system and depicting at least one test object is provided to a computer system. A signal absent image acquired with the imaging system, wherein the signal absent image does not depict the test object, is also provided to the computer system. A channelized signal present image and a channelized signal absent image is generated using the computer system to process the signal present image and the signal absent image, respectively, with a model observer. A biased detectability index is then estimated using the computer system to process the channelized signal present image and the channelized signal absent image. A non-stationary noise biased detectability index is estimated using the computer system to process a region of the channelized signal present image that does not contain the at least one test object and a spatially similar region in the channelized signal absent image. An unbiased detectability index is then generated with the computer system by subtracting the non-stationary noise biased detectability index from the biased detectability index.

The foregoing and other aspects and advantages described in the present disclosure will appear from the following description. In the description, reference is made to the accompanying drawings that form a part hereof, and in which there is shown by way of illustration a preferred embodiment. This embodiment does not necessarily represent the full scope of the invention, however, and reference is made therefore to the claims and herein for interpreting the scope of the invention.

BRIEF DESCRIPTION OF THE DRAWINGS

FIG. 3A depicts biased detectability indices, and FIG. 3B depicts detectability indices that have been bias corrected. In both FIGS. 3A and 3B, d' estimates with the open symbols represent linear fit intercepts.

DETAILED DESCRIPTION

Figure 1:
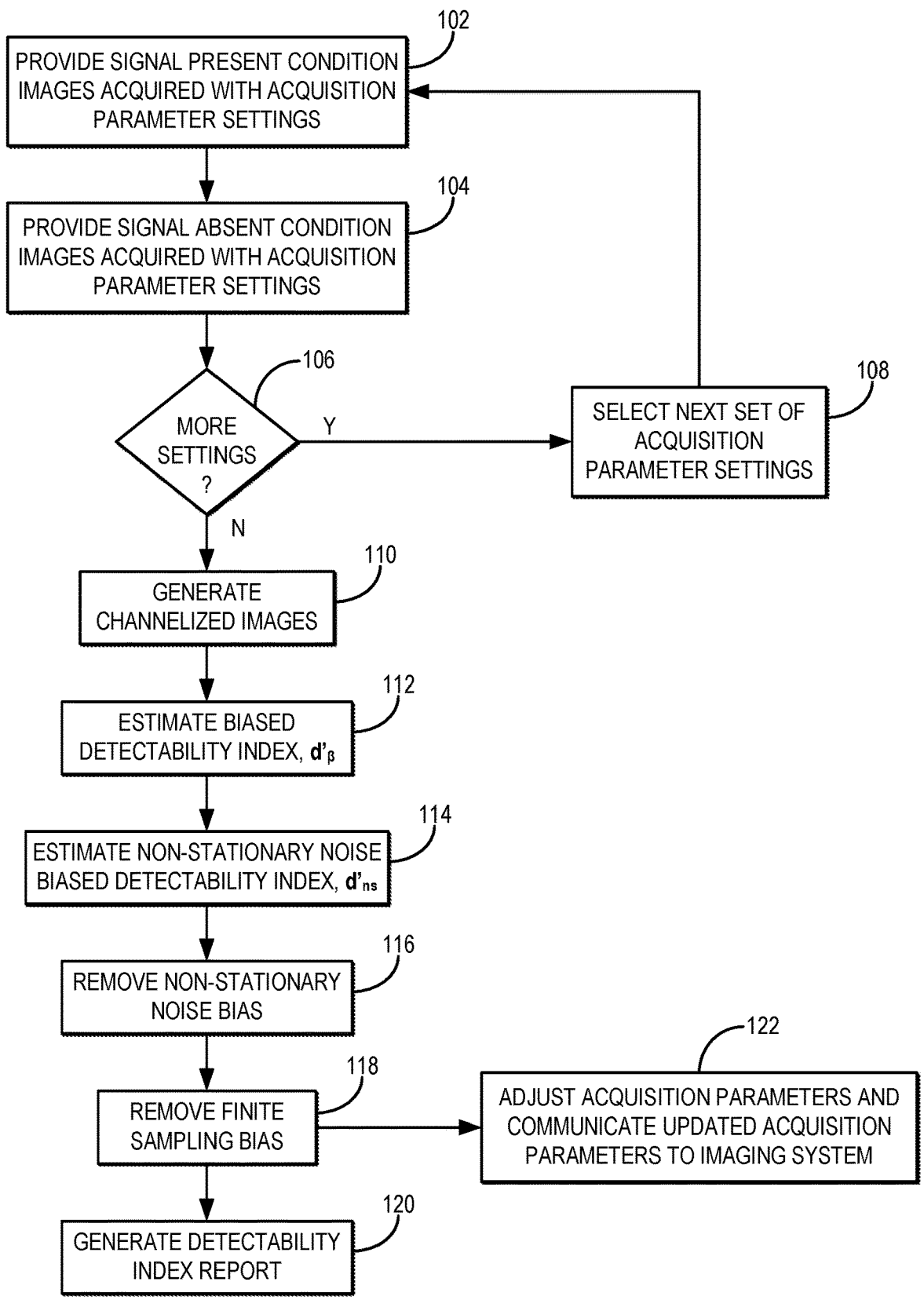
FIG. 1 is a flowchart setting forth the steps of an example method for correcting imaging system measurements for bias from non-stationary noise in model observers.

Described here are systems and methods for correcting measurements acquired with a medical imaging system for measurement bias from non-stationary noise in model observers. The medical imaging system may be an x-ray imaging system, but can also be a photographic system or other hardware-based imaging or detection system to which Hotelling-type statistical theory can be applied.

It is a discovery of the present disclosure that model observers based on Hotelling-type statistical theory suffer from positive bias due to non-random differences in the noise content of images acquired at different points in time. The systems and methods described here are capable of estimating and then correcting for this bias.

Using the systems and methods described here, real-time image acquisition guidance from accurate observer model figures of merit can be achieved and implemented. Observer models provide task-based figures of merit that can be used to quantify the quality of an image. Such tasks can include assessing the detectability of an object, the differentiability of two objects, and the classification of an object. It is contemplated that by accurately measuring figures of merit using observer models, clinically relevant quality thresholds can be generated for real-time image acquisition parameters in medical imaging procedures, such as x-ray angiography and fluoroscopy exams.

As one example, an accurate measurement of an object's detectability can be used for different fluoroscopic dose settings to determine the minimum detector dose necessary to reliably detect the object. This detector dose threshold could be implemented in the system's automated exposure rate control process, increasing the exposure rate if any region of the detector drops below the pre-defined threshold. Moreover, observer model-based image quality assessment incorporates all image components (spatial resolution, noise, etc.) into a comprehensive figure of merit. With this capability, object detectability/differentiability/classification thresholds can be fully parameterized with all aspects of image acquisition (e.g. dose, kVp, magnification factor, field of view, etc.—for x-ray fluoroscopy and angiography systems).

Development of comprehensive, clinically relevant thresholds for image acquisition parameters requires accurate quantification of tasked-based image quality metrics. Using the methods described here, accurate figures of merit can be generated across the entire spectrum of values (low to high), which can be utilized to generate the clinically relevant guidance thresholds.

Mathematical model observers have been previously implemented for assessing the performance of medical imaging systems. One example of such model observers is a channelized Hotelling model observer ("CHO"). In particular, application of a CHO requires that the noise properties of the imaging system to be stationary between samples. It will be appreciated that other statistical tests can also be employed in the methods described in the present disclosure. For instance, an Ideal Hotelling Observer ("IHO") could be used instead of a CHO.

For an object detection task, the CHO can be used to measure statistical differences between images acquired under two conditions: a condition in which a test object signal is present and a condition in which the test object signal is absent. For a given channelized image (v), the test statistic-of-interest derives from the natural logarithm of the likelihood ratio, which is the ratio of the probabilities that a sample, v, was generated from each of two experimental conditions. The generic test statistic is, $$\lambda = \Delta v^t K_v^{-1} v \qquad (1);$$

where $\Delta v$ is a channelized object signal, v is a channelized image, and $K_v$ is the interclass scatter matrix, which is the average of the covariance matrices of both the signal present and absent conditions. For each condition, the covariance matrices are calculated from the difference between the individual channelized images and the channelized expectation image for that condition. Individual test statistics for each image created under signal present and absent conditions can be calculated explicitly to create two distributions of test statistics $(\lambda_1, \lambda_2)$, which can be used to estimate a variety of performance metrics.

For practical implementations, the mean channelized object signal, $\Delta \bar{v}$, may be estimated as the difference between the average of many channelized signal present images, $\bar{v}_1$, and the average of many channelized signal absent images, $\bar{v}_2$. The mean of the corresponding distributions of signal present, $\bar{\lambda}_1$, and signal absent, $\bar{\lambda}_2$, test statistics can be calculated as, $$\bar{\lambda}_1 = \Delta \bar{v}^t K_v^{-1} \bar{v}_1 \qquad (2)$$

$$\bar{\lambda}_2 = \Delta \bar{v}^t K_v^{-1} \bar{v}_2 \qquad (3).$$

The first-order statistical properties of the two distributions of test statistics may be used to calculate a variety of figures of merit including area under a receiver-operator curve, percent correct for a multiple forced choice task, signal-to-noise ratio ("SNR"), or detectability index, d'. Detectability index is a special condition of SNR when the distributions for the two conditions are Gaussian and have equal variance. Detectability index is a simple linear combination of test statistics, thus providing the basis for direct and absolute comparison of distributions of $\lambda$, $$d' = \frac{\bar{\lambda}_1 - \bar{\lambda}_2}{\sqrt{\frac{1}{2}\sigma_{\lambda_1}^2 + \frac{1}{2}\sigma_{\lambda_2}^2}}; \qquad (4)$$

where it is useful to recognize that for Gaussian distributions of $\lambda$, $$d' = \sqrt{\Delta \bar{v}^t K_v^{-1} \Delta \bar{v}} = \sqrt{\Delta \bar{v}^t K_v^{-1} (\bar{v}_1 - \bar{v}_2)}. \qquad (5)$$

By substitution with Eqns. (2) and (3), Eqn. (5) becomes, $$d' = \sqrt{\bar{\lambda}_1 - \bar{\lambda}_2} = \sqrt{\Delta \bar{\lambda}}. \qquad (6)$$

Experimental estimates of detectability index have been previously shown to include bias due to finite sampling. In brief, the model's template, including both the object signal, $\Delta \bar{v}$, and interclass scatter matrix, $K_v$, is non-ideal and contaminated with noise from the finite image sets that are used to derive it. By one method of calculating the detectability index, d', the same sets of images are used to train and test the model (i.e. the same images used to create the template, $\Delta \bar{v}^t K_v^{-1}$, are used calculate the mean test statistics in Eqns. (2) and (3)). This method is known as the "resubstitution" method, and is described for example by K. Fukunaga and R. R. Hayes in "Effects of sample size in classifier design," *IEEE Transactions on Pattern Analysis and Machine Intelligence*, 11(8):873-885 (1989); by H. P. Chan, et al., in "Classifier design for computer-aided diagnosis: Effects of finite sample size on the mean performance of classical and neural network classifiers", *Med. Phys.*, 2654-2668 (1999); by B. D. Gallas in "Variance of the channelized-Hotelling observer from a finite number of trainers and testers," *Proc. SPIE* 5034, 100-111 (2003); and by R. M. Gagne, et al., in "Toward objective and quantitative evaluation of imaging systems using images of phantoms," *Med. Phys.*, 33(1):83-95 (2006).

An alternative "holdout" method uses unique image samples to train and test the model, as described for example by K. Fukunaga and R. R. Hayes in "Effects of sample size in classifier design," *IEEE Transactions on Pattern Analysis and Machine Intelligence*, 11(8):873-885 (1989); and by B. D. Gallas in "Variance of the channelized-Hotelling observer from a finite number of trainers and testers," *Proc. SPIE* 5034, 100-111 (2003).

Both methods to calculate the detectability index suffer from finite sampling bias. The resubstitution method introduces positive bias and the holdout method introduces negative bias. It has been shown that finite sampling bias can be corrected experimentally from a finite dataset by varying the number of sample images, n, calculating d'(n), and performing a linear fit of d'(n) versus 1/n. The intercept of the linear fit provides an estimate of $d'_\infty$, which is the detectability index expected for an experiment in which $n=\infty$, thus providing a finite sampling bias-free estimate of d'.

The linear fit method described above to estimate $d'_\infty$, however, still includes positive bias. Specifically, the estimated $d'_\infty$ values still trend to a low value, but not toward zero for small test objects and low DTD conditions.

It is a discovery of the invention that previously unrecognized mechanism for the bias in $d'_\infty$ estimates described above is due to non-random differences in noise content between images acquired at different times, which may be referred to as temporally variable non-stationary noise. Consequently, this bias is unrelated to finite sampling and cannot be managed by increasing the number of training samples. Provided that the net signal from non-stationary noise is different between the signal present versus signal absent conditions, it would demonstrate as an additive signal in the CHO model such that the experimentally estimated d' inherently includes contributions from the signal of the test object. The univariate probability density function describing these two signal sources is given by, $$f(x) = \frac{1}{\sqrt{2\pi\sigma^2}} e^{-\frac{((x_o + x_{ns}) - (\overline{x}_o + \overline{x}_{ns}))^2}{\sigma^2 2}}; \quad (7)$$

where $x_o$ is the signal from the test object, $x_{ns}$ is the signal due to differences in temporally variable non-stationary noise between the two test conditions, and $\sigma^2$ is the variance of both distributions of x. The multivariate Hotelling observer detectability index for these two signal sources is given by, $$\sqrt{\Delta\overline{\lambda}} = \sqrt{\Delta\overline{v}_o^t K_{o,ns}^{-1} \Delta\overline{v}_o} + \sqrt{\Delta\overline{v}_{ns}^t K_{o,ns}^{-1} \Delta\overline{v}_{ns}}; \quad (8)$$

where $\Delta\overline{v}_o$ and $\Delta\overline{v}_{ns}$ are the multivariate vector mean differences between signal present and absent conditions associated with the test object and non-stationary noise signals, respectively, and $K_{o,ns}$ is the interclass scatter matrix of the two conditions. By substitution with Eqns. (5) and (6), Eqn. (8) can be rewritten as, $$d'_\beta = d'_o + d'_{ns}; \quad (9)$$

where, $$d'_\beta = \sqrt{\Delta\overline{\lambda}}; \quad (10)$$

$$d'_o = \sqrt{\Delta\overline{v}_o^t K_{o,ns}^{-1} \Delta\overline{v}_o}; \quad (11)$$

$$d'_{ns} = \sqrt{\Delta\overline{v}_{ns}^t K_{o,ns}^{-1} \Delta\overline{v}_{ns}}. \quad (12)$$

In this nomenclature, $d'_o$ is the detectability index due to the presence of the test object, $d'_{ns}$ is the detectability index due to temporally variable non-stationary noise, and $d'_\beta$ is the biased d' estimate calculated by straightforward application of the CHO to image sets that include temporally variable non-stationary noise. Because it is typically desired to measure the detectability index of the imaging system in the presence of a test object, Eqn. (9) can be solved for $d'_o$ as, $$d'_o = d'_\beta - d'_{ns} \quad (13).$$

Provided that $d'_{ns}$ can be estimated directly using Eqns. (1)-(4) applied to two sets of test object absent images ($d'_o$=0), Eqn. (13) can be used to estimate test object detectability indices independent of bias due to temporally variable non-stationary noise. The systems and methods described here can thus be used to first perform direct estimation and correction of bias due to non-stationary noise per Eqn. (13), and then to also perform the known method of estimating $d'_\infty$ by linear fit of $d'_o(n)$ versus 1/n to remove bias due to finite sampling.

Referring now to FIG. 1, a flowchart is illustrated as setting forth the steps of an example method for generating an unbiased detectability index for an imaging system. The method includes providing one or more images acquired with the imaging system, under two different conditions, to a computer system. The first condition corresponds to a signal present condition, and the one or more images, $x_o$, acquired under this condition are provided to the computer system at step 102. The second condition corresponds to a signal absent condition, and the one or more images, $x_{ns}$, acquired under this condition are provided to the computer system at step 104.

The images, $x_0$, acquired under the signal present condition can be acquired by imaging a test object phantom with the imaging system. As one example, a test object phantom can include cylindrical objects with their central axis aligned with the x-ray beam and which appear as disk-shaped objects in an x-ray image. As another example, a test object phantom can include cylindrical objects with their central axis aligned orthogonal to the x-ray beam and which appear as a rod-shaped object in an x-ray image. As another example, the test object phantom can include spheres of various diameters, such as 0.5-4.0 mm. The test phantom object can also include a pill capsule shape, where the length of the mid-section is equal to its diameter. As still another example, the test object phantom can be a rod-shaped object with hemispherical ends whose mid-section length is equal to the diameter of the rod. An example of such a rod-shaped object could have an overall length of 30 mm, for example. A variety of physical shapes and orientations of test object phantoms may be appropriate to support a variety of x-ray or non-x-ray based imaging systems. In general, other test objects that mimic intravascular guidewires, catheters, stents, and other intravascular diagnostic and therapeutic devices can also be used.

The test object phantom can be stationary when imaged, or can be moving when images. As one example, the test object phantom (or multiple test object phantoms) can be coupled to a support that rotates, translates, oscillates, or combinations thereof, during imaging. Imaging a moving test object phantom can be advantageous for real-time imaging applications, such as imaging cardiovascular structures that may have instantaneous velocities as high as 30 cm/s.

As determined at decision block 106 and indicated at step 108, additional images acquired using different acquisition parameters can also be provided to the computer system. For examples in which the imaging system is an x-ray imaging system, the peak tube potential, x-ray pulse duration, and current can be controlled by an automatic exposure rate control circuit to achieve various different detector target dose ("DTD") settings. Images with a test object phantom in a fixed spatial location or variable locations, and with the test object absent, can be acquired incrementally using specified detector target dose values, such as for example between 6 and 240 nGy. For each DTD setting, multiple images can be acquired. As one example, cine images can be acquired using a specified frame rate (e.g., 30 frames per second).

Channelized images are then generated from the provided images, $x_0$, as indicated at step 110. Thus, for example, a channelized image can be generated for each condition (i.e., signal present, signal absent) at each set of acquisition parameters (e.g., each DTD value). In some instances, the channelized images are generated by extracting regions-of-interest (e.g., regions containing objects in the test object phantom) from the provided images and channelizing the subvolumes containing the regions-of-interest. As one example, the regions-of-interest can be channelized using q=96 Gabor functions.

A biased detectability index, $d'_\beta$, can then be estimated based on the channelized images, as indicated at step 112. For example, the biased detectability index, $d'_\beta$, can be estimated using Eqns. (1)-(10). A non-stationary noise detectability index, $d'_{ns}$, is then estimated, as indicated at step 114. This non-stationary noise detectability index, $d'_\beta$, represents bias in the measurement due to the presence of non-stationary noise and can be estimated from a region-of-interest in the signal present images and the signal absent images that does not include an object (e.g., the 0.0 mm object region of a test phantom image). This non-stationary noise biased detectability index, $d'_{ns}$, can be estimated in the same manner as the biased detectability index, $d'_\beta$, estimated in step 112, but for using the different region of the signal present images and the signal absent images as the basis for the estimation. Alternatively, multiple sets of signal-absent images may be acquired and used to estimate non-stationary noise detectability index, $d'_\beta$, at any spatial location within the signal absent images. The non-stationary noise biased detectability index, $d'_{ns}$, can be estimated once or multiple times for each set of acquisition parameters (e.g., each DTD value).

The non-stationary noise bias is then removed from the biased detectability index, $d'_\beta$, to generate a first unbiased detectability index, $d'_o$, by subtracting the non-stationary noise detectability index, $d'_{ns}$, from the biased detectability index, $d'_\beta$, as indicated at step 116. The provided images can be resampled to a number of different samples, and the foregoing process repeated to generate values of $d'_o$ for different numbers of samples, n. An unbiased detectability index, $d'_{\infty,o}$, can then be estimated by linear fitting $d'_o(n)$ versus 1/n, to remove bias from finite sampling, as indicated at step 118.

A report can then be generated based on the unbiased detectability index, $d'_{\infty,o}$, as indicated at step 120. This report can provide useful information about the imaging system for which the unbiased detectability index, $d'_{\infty,o}$, was generated. In some instances, a number of different unbiased detectability indices, $d'_{\infty,o}$, are generated (e.g., one for each different set of acquisition parameters or DTD values) and the report can provide information about acquisition parameters settings that will optimize detectability for the imaging system in question. In some instances, acquisition parameters can be adjusted based on the unbiased detectability index, $d'_{\infty,o}$, or indices, and these updated acquisition parameters communicated to the imaging system for an updated imaging session, as indicated at step 122.

Figure 2:
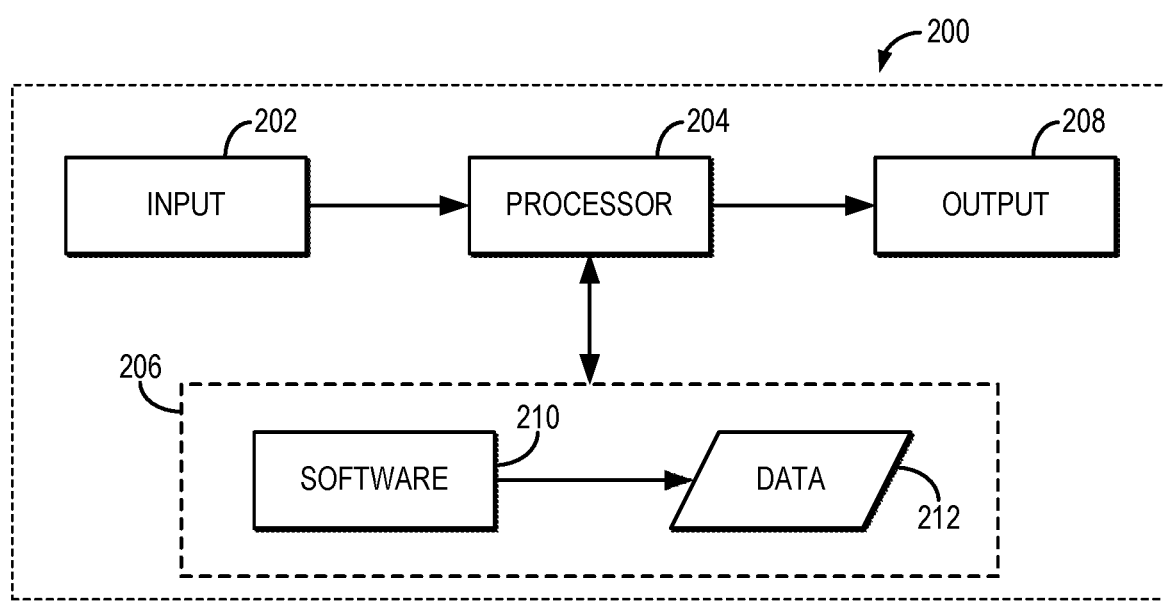
FIG. 2 is a block diagram of an example computer system that can implement the methods described here.

Referring now to FIG. 2, a block diagram of an example computer system 200 that can implement the methods described above is shown. In some embodiments, the computer system may form a part of a medical imaging system or other imaging system.

The computer system 200 generally includes an input 202, at least one processor 204, a memory 206, and an output 208. The computer system 200 can also include any suitable device for reading computer-readable storage media. The computer system 200 may be, for example, a workstation, a notebook computer, a tablet device, a mobile device, a multimedia device, a network server, a mainframe, or any other general-purpose or application-specific computing device. The computer system 200 may operate autonomously or semi-autonomously, or may read executable software instructions from the memory 206 or a computer-readable medium (e.g., a hard drive, a CD-ROM, flash memory), or may receive instructions via the input 202 from a user, or any another source logically connected to a computer or device, such as another networked computer or server. In general, the computer system 200 is programmed or otherwise configured to implement the methods and algorithms described above.

The input 202 may take any suitable shape or form, as desired, for operation of the computer system 200, including the ability for selecting, entering, or otherwise specifying parameters consistent with performing tasks, processing data, or operating the computer system 200. In some aspects, the input 202 may be configured to receive data, such as images acquired with an imaging system, which may be a medical imaging system. These images may be processed as described above. In addition, the input 202 may also be configured to receive any other data or information considered useful for estimating and correcting for imaging system measurement bias from non-stationary noise in model observers using the methods described above.

Among the processing tasks for operating the computer system 200, the at least one processor 204 may also be configured to receive data, such as images acquired with an imaging system, which may be a medical imaging system. In some configurations, the at least one processor 204 may also be configured to carry out any number of post-processing steps on data received by way of the input 202. In addition, the at least one processor 204 may be capable of generating reports based on generated, unbiased detectability indices, as described above, and may also be capable of adjusting acquisition settings of an imaging system.

The memory 206 may contain software 210 and data 212, and may be configured for storage and retrieval of processed information, instructions, and data to be processed by the at least one processor 204. In some aspects, the software 210 may contain instructions directed to estimating and correcting for bias in imaging system measurements from non-stationary noise in model observers, generating unbiased detectability indices, generating reports based on such detectability indices, and adjusting acquisition settings for an imaging system. Also, the data 212 may include any data necessary for operating the computer system 200, and may include any suitable images as described above.

In addition, the output 208 may take any shape or form, as desired, and may be configured for displaying, in addition to other desired information, images, maps of detectability indices, and reports generated based on biased and unbiased detectability indices.

Although the methods described here have been described with respect to correcting for measurement bias in an imaging system, it will be appreciated by those skilled in the art that the methods can be implemented for other measurement systems, too. For example, the methods can be implemented for measurement systems that detect or classify signal data, which may include optical signal data (e.g., light-based signals), acoustic signal data (e.g., sound-based signals), or electromagnetic signal data (e.g., radio frequency wave signals).

Example Study

In an example study, a channelized Hotelling model observer ("CHO") method was implemented to assess performance of an x-ray angiography system. The analytical methods included correction for known bias error due to finite sampling. Detectability indices (d') corresponding to cylindrical shaped objects that create disk-shaped objects in the images with diameters in the range 0.5 to 4 mm were calculated. Application of the CHO for variable detector target dose ("DTD") in the range 6 to 240 nGy per frame resulted in d' estimates which were as much as 2.9 times greater than expected of a quantum limited system. Overestimation of d' less than about 3.0 was presumed to be a result of bias error due to temporally variable non-stationary noise.

A statistical methodology that allowed for independent contributions of signal from a test object ("o") and temporally variable non-stationary noise ("ns") was implemented. The methodology demonstrated that the biased detectability index, $d'_\beta$, is the sum of the detectability indices associated with the test object, $d'_o$, and non-stationary noise, $d'_{ns}$. Given the nature of the imaging system and the experimental methods, $d'_o$ cannot be directly determined independent of $d'_{ns}$. However, methods to estimate $d'_{ns}$ independent of $d'_o$ were developed and implemented. In accordance with the methodology, $d'_{ns}$ was estimated and subtracted from experimental estimates of $d'_\beta$, thereby providing an unbiased estimate of $d'_o$. Estimates of $d'_o$ exhibited trends consistent with expectations of an angiography system that is quantum limited for high DTD and compromised by detector electronic readout noise for low DTD conditions.

Methods

Cylindrical Object Phantom.

A 2.5 mm thick polymethyl methacrylate (PMMA) test object phantom containing 7 cylindrical objects of height 2.5 mm and diameters 0.5, 0.75, 1.0, 1.5, 2.0, 3.0, and 4.0 mm was constructed. The cylindrical objects were arranged circumferentially upon a 2.5 cm radius and milled into the PMMA sheet at an angle of 1.9 degrees with respect to a perpendicular axis passing through the center of the phantom. This angle ensured that the walls of the cylinders were parallel to the x-ray beam when the phantom was positioned 75 cm from an x-ray focal spot. Projection of the x-ray shadow of the test object produced disk-shaped objects in the image plane. An 8th region of the phantom was left void of a cylindrical test object (diameter=0.0 mm) and used to directly estimate $d'_{ns}$ for each experimental condition. The test object phantom also included three 1 mm diameter stainless steel spheres as fiducial markers.

Image Acquisition.

The test object phantom was placed in the center of a 25 cm stack of PMMA x-ray absorption and scatter phantom. A 5 mm void was left in the center of the thickness of the PMMA stack so that the test object phantom could be replaced with a 2.5 mm blank PMMA sheet without disturbing the 25 cm thick PMMA stack. Images were acquired using an x-ray angiography system. The active layer of the x-ray detector was crystalline CsI. The pixel pitch of the detector was 0.184 mm and the nominal diagonal length of the detector was 25 cm. A nominal 20 cm diagonal field of view is routinely used clinically and was specified for these experiments. A 0.3 mm copper x-ray beam spectral filter was used. The peak tube potential, x-ray pulse duration and current were controlled by the automatic exposure rate control circuit to achieve the specified detector target dose. Images of the test object phantom in a fixed spatial location were acquired incrementally using specified detector target dose values between 6 and 240 nGy. Images corresponding to DTD=0 nGy (no x-ray exposure) were also acquired. These images contained only detector electronic readout noise. The x-ray system was configured to export unprocessed images with 512×512, 8 bit pixel matrices.

The x-ray source to test object phantom distance was 75 cm and the x-ray source to detector distance was 100 cm. For each DTD, 4×10 second cine images were acquired using frame rate 30 fps. In this manner, 1204 signal present image frames were acquired for each DTD, including DTD=0 nGy. The cylindrical test object phantom was replaced by a 2.5 mm thick PMMA blank and a series of signal absent images was acquired to exactly compliment the images containing the cylindrical test object phantom.

As described above, the systems and methods described here estimate $d'_{ns}$ bias at one location within the images and use this single location value to estimate $d'_o$ at the other test object locations within the images. This method utilizes $d'_{ns}$ estimates that are independent of location within the images. For other implementations, it may be appropriate to measure $d'_{ns}$ at different or at multiple locations within the images.

Data Analysis and CHO Application.

For each DTD, the average of 1204 the test object phantom images was calculated. The subpixel location of the fiducial markers was determined using a threshold-based detection algorithm. The locations of the fiducial markers were referenced to algorithmically determine the location of the centers of the individual test objects. For each object size (including the 0.0 mm object), 101×101 pixel (27.9×27.9 mm2 at the object plane) regions with centers corresponding to the center of each object were extracted from each of the 1204 signal present images. Corresponding regions were extracted from each of the 1204 signal absent images. Each of the 2×8×1204 regions were channelized using q=96 Gabor functions as described by C. P. Favazza, et al., in "Implementation of a channelized Hotelling observer model to assess image quality of x-ray angiography systems," *J. Med. Imag.*, 2(1): 015503, (2015).

Resampling methods were adapted to estimate $d'_\infty$. For each object size, including the 0.0 mm "object," the collection of 1204 channel responses was resampled without replacement p=1, 2, 4, and 8 times using subsets of n=1204, 602, 301, and 151 samples, respectively, and used to calculate $d'_\infty$ by the resubstitution method described above. For the maximum number of 1204 images, resampling was performed once and $d'_{n=1204}$ was calculated once. When the number of images resampled was 602, 301, and 151, resampling was performed 2, 4, 8 times, resulting in 2, 4, and 8 estimates of d'. The same number of image samples (n) were used to both create the template and test the image sets to estimate $d'_n$. When d' was estimated using the holdout method, the object size-specific collections of 1204 channelized regions were resampled without replacement p=1, 2, and 4 times using subsets of n=602, 301, and 151 samples. For each sampling method, the mean d' for each of the p iterations was calculated and used as input to perform linear fit of d'(n) versus 1/n, the intercept of which was assigned as $d'_\infty$.

From a given set of 2×1204 images corresponding to a given DTD, $d'_\infty$ was calculated 4× for each of the seven real test objects. Calculations of $d'_\infty$ were performed using both the resubstitution and holdout sampling strategies and both the presumably biased standard method and bias corrected method. Bias due to non-stationary noise ($d'_{ns}$) was calculated from the 0.0 mm object region of the images using the same processes as for the seven real objects. In this manner, $d'_{ns}$ was estimated once for each DTD and resampled image subset (p and n). These unique $d'_{ns}$ estimates were subtracted from the biased $d'_\beta$ estimates of each real object to calculate $d'_o$. Thus, $d'_{ns}$ was subtracted from $d'_\beta$ prior to linear fitting $d'_o(n)$ versus 1/n to calculate the linear fit intercept, $d'_{\infty,o}$.

Results

Considering the detector target dose range 6 to 240 nGy, the peak tube potential ranged from 93.6 to 96.2 kVp, pulse duration from 3.5 to 9.2 ms, and current from 9 to 246 mA. The difference between the average of 1204 images of the cylindrical object phantom and 1204 signal absent images acquired using 120 nGy per image is shown in FIG. 1.

Figure 3A:
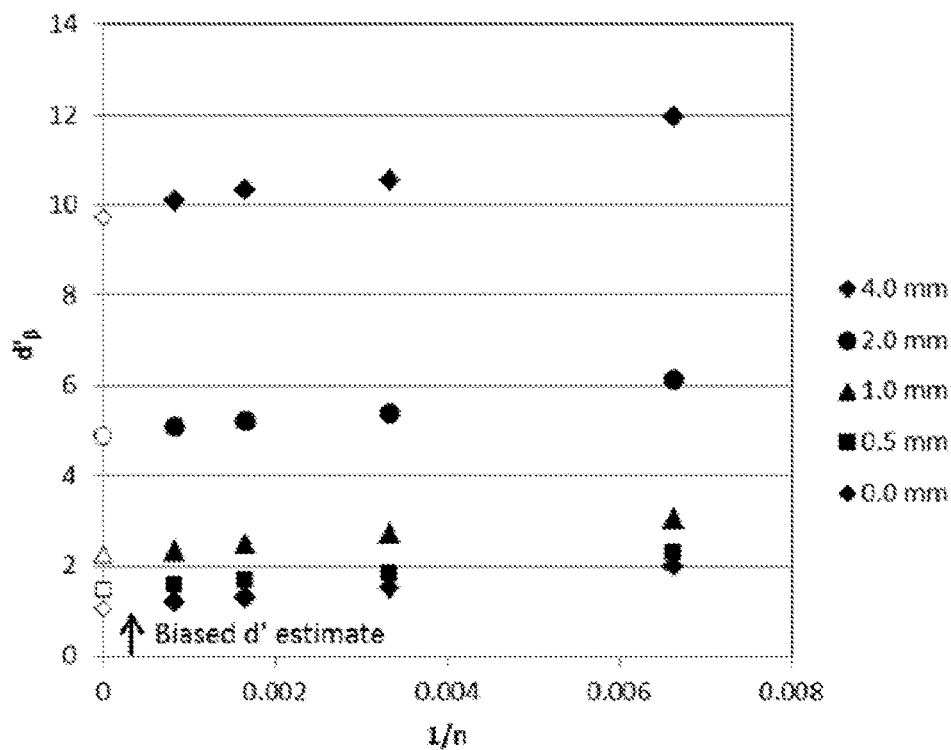
FIGS. 3A and 3B show detectability indices d' for detector target dose 18 nGy and object sizes ranging from 0.0 to 4.0 mm calculated using a resubstitution method of resampling.
Figure 3B:
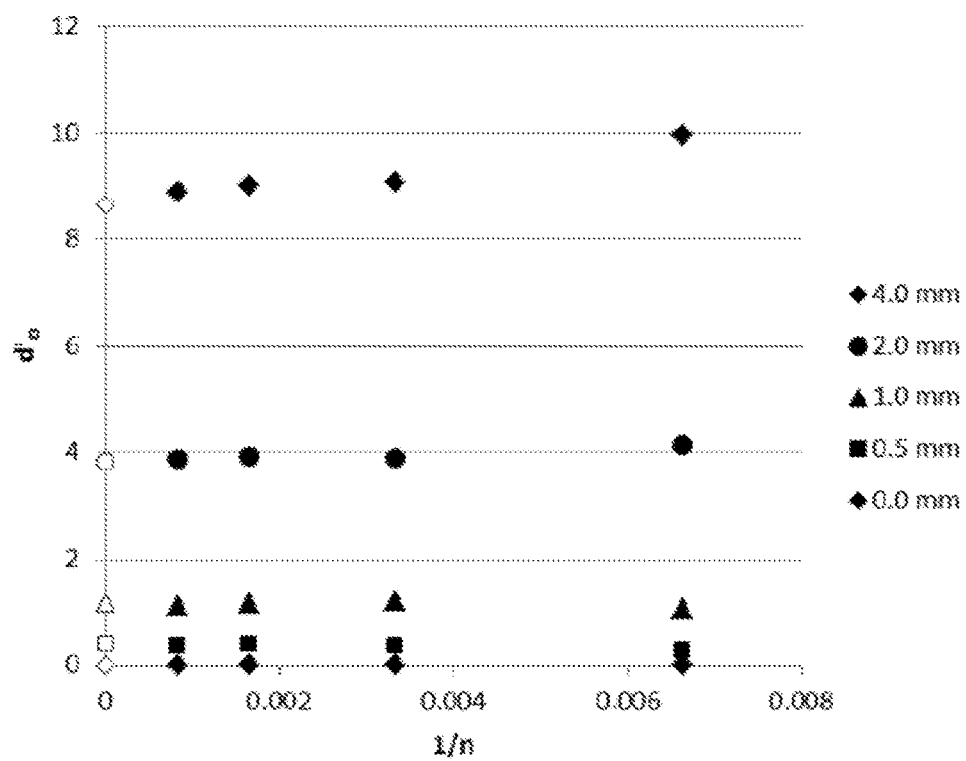

Sample $d'\beta$ and $d'o$ are shown in FIGS. 3A and 3B, respectively, for DTD=18 nGy, object diameters 4.0, 2.0, 1.0, and 0.5 and 0.0 mm (d'ns), and using the resubstitution method. Data points represent the mean of "p" estimates for a given "n" which were used to calculate the linear fit intercept. Data in FIG. 3a were generated using the presumably biased $d'\beta$ estimates, whereas data in FIG. 3b were generated using the bias-corrected d'o estimates. The data points at 1/n=0 represent the linear fit intercepts d'∞. In particular, it can be seen that d'ns corresponding to the 0.0 mm object is associated with a positive $d'\beta$ estimate in FIG. 3A, whereas the expected values for this condition was d'=0.

FIG. 3B demonstrates reduction in the d' estimates following removal of bias using the methods described above. For each 1/n and all object sizes, d'ns was subtracted from $d'\beta$ prior to performing the linear fit.

Figure 4:
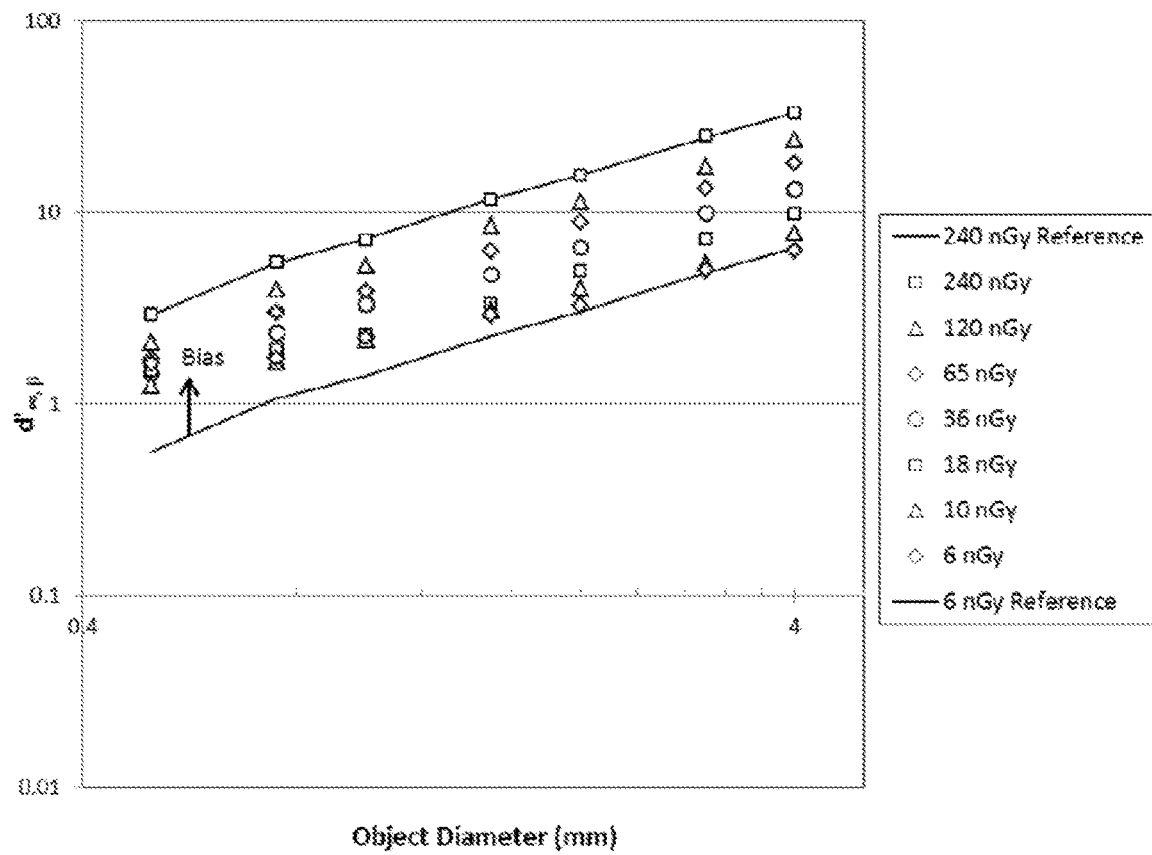
FIG. 4 shows biased $d'_\infty$ estimates calculated using a resubstitution method of resampling.

FIG. 4 shows $d'_{\infty,\beta}$ as a function of object size for all DTD levels and calculated using the resubstitution method. The $d'_{\infty,\beta}$ estimates calculated using the holdout method were equivalent and, therefore, detailed results using the holdout method were not presented graphically. The reference lines in FIG. 4 indicate the expected bias-corrected d'∞ for the DTD=240 nGy and 6 nGy for a quantum limited system and assuming that the 240 nGy condition accurately estimates d'∞ for all object sizes. Specifically, the 240 nGy reference line directly represents the 240 nGy measurements and the 6 nGy reference line was scaled by (Q'6 nGy/Q'240 nGy)0.5. The reference lines deviate from log-linear due to the relative influence of imaging system blur on small versus large objects. That the data in FIG. 4 does not trend in proportion to the reference lines for low $d'_{\infty,\beta}$ conditions (low DTD and small diameter objects) is a result of bias error in the estimates of $d'_{\infty,\beta}$.

Preliminary experiments that utilized two sets of signal absent images to assess variability of $d'_{\infty,ns}$ at 8 locations within the images demonstrated that $d'_{\infty,ns}$ was invariant to location within the images. For each DTD, the standard deviation of $d'_{\infty,ns}$ estimates calculated at 8 locations within the images was proportional to the magnitude of the $d'_{\infty,ns}$ estimate. Considering all DTD levels, the average percent standard deviation of the 8 $d'_{\infty,ns}$ estimates was 10.5±2.1% (7.0 to 15.1%) using the resubstitution method and 18.6±9.1% (10.0 to 37.2%) using the holdout method.

Figure 5:
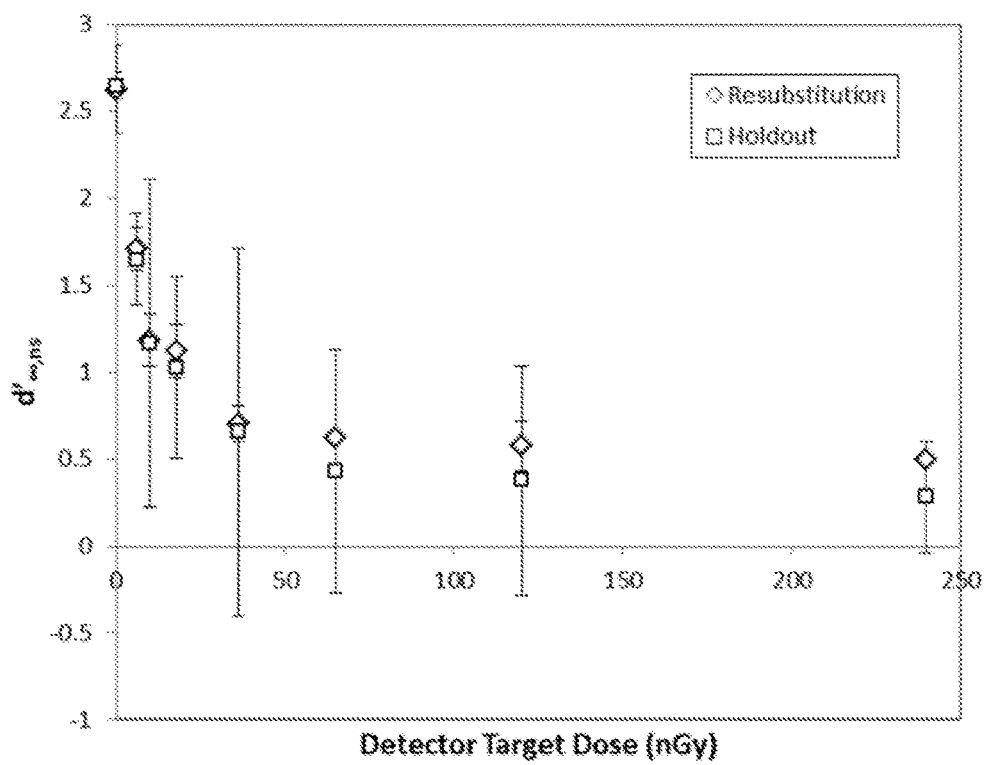
FIG. 5 shows $d'_\infty$ bias estimates calculated using both resubstitution and holdout resampling methods. $d'_\infty$ for DTD=0 is due to non-stationary detector electronic readout noise.

FIG. 5 shows single image location estimates of $d'_{\infty,ns}$ as a function of DTD, including DTD=0. The values in FIG. 5 were calculated using the 0.0 mm object region of the image sets containing the test phantom. The $d'_{\infty,ns}$ values were maximum for DTD=0 and decreased monotonically with DTD due to increasing contribution of x-ray quantum noise with increasing DTD.

Considering all non-zero DTD estimates of $d'_{\infty,ns}$, the relative magnitude of the 95% CIs of the $d'_{\infty,ns}(n)$ versus 1/n linear fit estimates was 11.5±5.7% (3.8 to 19.5%) for the resubstitution method results in FIG. 5 and was 77±71% (14 to 200%) for the holdout method.

Figure 6:
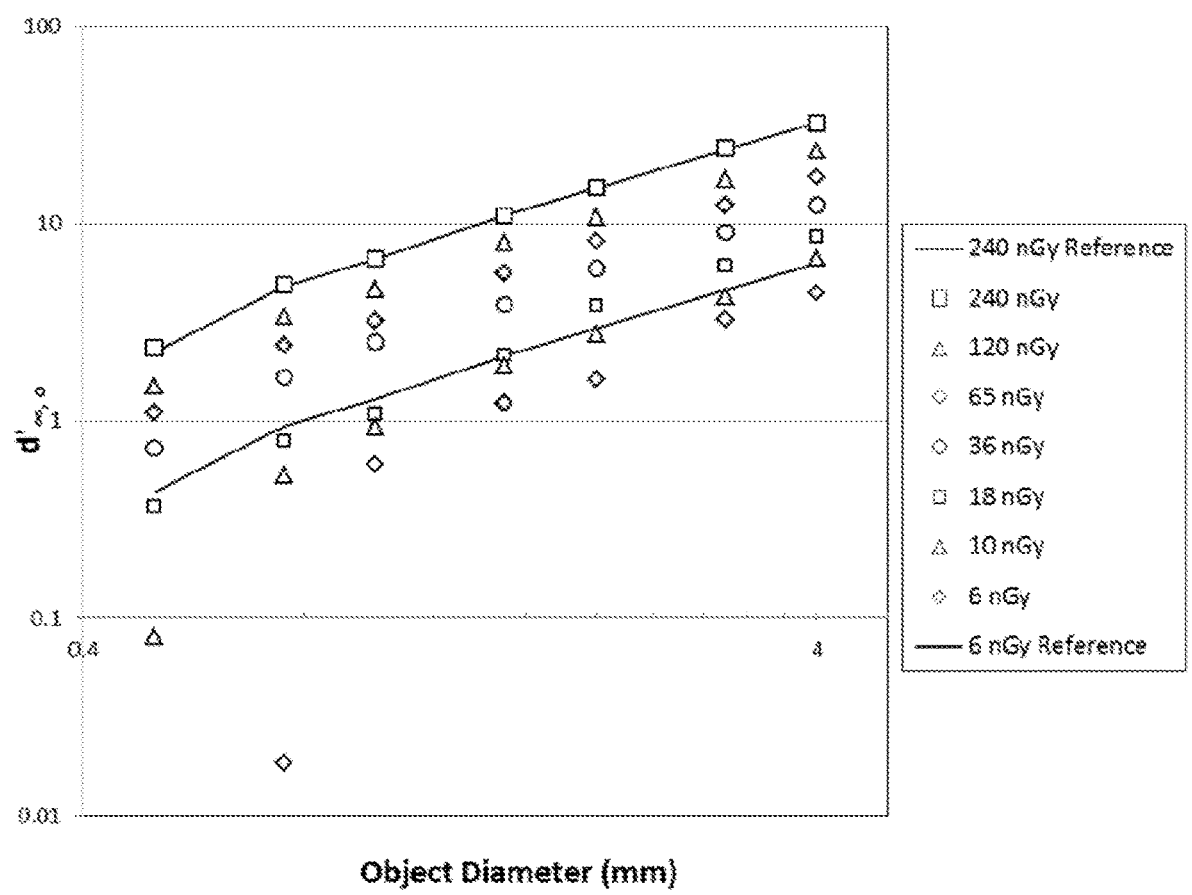
FIG. 6 shows bias corrected $d'\infty$ estimates calculated using the resubstitution method of resampling and the methods described herein.

FIG. 6 shows bias corrected $d'_{\infty,o}$ values calculated using the resubstitution method and the methods described above. Compared to $d'_{\infty,\beta}$ presented in FIG. 4, $d'_{\infty,o}$ demonstrates trends as expected of a quantum limited imaging system for high and mid-range DTD conditions. The sub-quantum limited estimates of $d'_{\infty,o}$ for low DTD and small objects are consistent with detrimental effects of detector electronic readout noise. The $d'_{\infty,o}$ value for the 0.5 mm object and DTD=6 nGy was negative and not included in FIG. 6.

Considering all data points in FIG. 6 greater than 1.0, the average relative magnitude of the 95% CIs of the $d'_{\infty,o}(n)$ vs. 1/n linear fit estimates was 10% (range 1 to 53%), with greater relative error associated with smaller estimates of $d'_{\infty,o}$. Relative error was greater for $d'_{\infty,o} \le 1.0$.

Considering all biased estimates of $d'_{\infty,\beta}$ calculated using the resubstitution method, the ratio $d'_{\infty,\beta}/d'_{\infty,QL}$ was in the range 0.94 to 2.9. For this metric, values greater than 1.0 indicate experimental estimates relatively greater than would be expected for a quantum limited system. For the biased $d'_{\infty,\beta}$ estimates, the ratios increased with decreasing DTD and object size.

Considering all non-negative estimates of $d'_{\infty,o}$ the ratio was in the range 0.02 to 1.06. This ratio was approximately 1.0 for detector target dose 240 and 120 nGy and decreased with decreasing DTD and object size. The average difference in $d'_\infty/d'_{QL}$ for the resubstitution versus holdout methods was 0.00±0.02 (−0.05 to 0.09).

Results suggest that the methods described here provide $d'_o$ estimates that are accurate and precise for $d'_o \ge \sim 1.0$. Further, results demonstrated that the source of bias was detector electronic readout noise. In summary, this systems and method described here are capable of testing for and estimating the presence of bias in Hotelling model observers due to temporally variable non-stationary noise and for correcting this bias.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating an unbiased detectability index from images acquired with an imaging system, the method comprising:
    (a) providing to a computer system a signal-present image acquired with an imaging system depicting at least one test object;
    (b) providing to the computer system a signal-absent image acquired with the imaging system, wherein the signal-absent image does not depict the at least one test object;
    (c) generating a processed signal-present image and a processed signal-absent image using the computer system to implement a model observer to operate directly on the signal-present image and the signal-absent image, respectively;
    (d) estimating a biased detectability index from the processed signal-present image and the processed signal-absent image using the computer system;
    (e) estimating a non-stationary noise detectability index using the computer system to process a region of the processed signal-present image that does not contain the at least one test object and a spatially similar region in the processed signal-absent image; and
    (f) generating an unbiased detectability index with the computer system by subtracting the non-stationary noise detectability index from the biased detectability index.

2. The method as recited in claim 1, wherein step (f) includes:
    generating unbiased detectability indices for a plurality of different sample numbers; and
    removing a finite sampling bias from the unbiased detectability index by using the computer system to linear fit the unbiased detectability indices as a function of the plurality of different sample numbers versus an inverse of the plurality of different sample numbers.

3. The method as recited in claim 1, further comprising: generating a report based on the unbiased detectability index, the report indicating an assessment of a detectability with the imaging system.

4. The method as recited in claim 1, further comprising: adjusting acquisition parameters of the imaging system based on the generated unbiased detectability index.

5. The method as recited in claim 4, further comprising: acquiring an image with the imaging system using the adjusted acquisition parameters.

6. The method as recited in claim 4, wherein the imaging system is an x-ray imaging system, and the adjusting the acquisition parameters of the x-ray imaging system comprises maximizing the unbiased detectability index white minimizing a detector target dose (DTD).

7. The method as recited in claim 1, wherein step (c) includes:
generating a channelizing signal-present image and a channelized signal-absent image by channelizing the signal-present image and the signal-absent image.

8. The method as recited in claim 1, wherein step (c) includes implementing the model observer to operate directly on a derivative of the signal-present image and a derivative of the signal-absent image.

9. A method for generating an unbiased detectability index from measurement data acquired with a measurement system, the method comprising:
(a) providing to a computer system signal-present data acquired with a measurement system, wherein the signal-present data are indicative of a presence of at least one test object;
(b) providing to the computer system signal-absent data acquired with the measurement system, wherein the signal-absent data are indicative of an absence of the at least one test object;
(c) generating processed signal-present data and processed signal-absent data with the computer system by implementing a model observer that operates directly on the signal-present data and the signal-absent data, respectively;
(d) estimating a biased detectability index from the processed signal-present data and the processed signal-absent data using the computer system;
(e) estimating a non-stationary noise detectability index using the computer system to process a region of the processed signal-present data that does not contain data indicative of the at least one test object and a spatially similar region in the processed signal-absent image; and
generating an unbiased detectability index with the computer system by subtracting the non-stationary noise detectability index from the biased detectability index.

10. The method as recited in claim 9, wherein step (c) includes:
generating channelized signal-present data and channelized signal-absent data by channelizing the signal-present data and the signal-absent data.

11. The method as recited in claim 9, wherein step (c) includes:
implementing the model observer to operate directly on a derivative of the signal-present data and a derivative of the signal-absent data.

12. The method as recited in claim 9, wherein the measurement system performs at least one of a detection or a classification of signal data selected from the group consisting of optical signal data, acoustic signal data, and electromagnetic signal data.

13. The method as recited in claim 12, wherein the electromagnetic signal data includes signal data associated with radio-frequency waves.

* * * * *

UNITED STATES PATENT AND TRADEMARK OFFICE
CERTIFICATE OF CORRECTION

| | |
|---|---|
| PATENT NO. | : 11,058,392 B2 |
| APPLICATION NO. | : 16/471526 |
| DATED | : July 13, 2021 |
| INVENTOR(S) | : Kenneth A. Fetterly et al. |

It is certified that error appears in the above-identified patent and that said Letters Patent is hereby corrected as shown below:

In the Specification

Column 7, Line 6, "$d'_\beta$" should be --$d'_{ns}$--.

Column 7, Line 18, "$d'_\beta$" should be --$d'_{ns}$--.

In the Claims

Column 13, Claim 6, Line 17, "white" should be --while--.

Column 14, Claim 9, Line 15, "generating" should be --(f) generating--.

Signed and Sealed this
Third Day of May, 2022

*Katherine Kelly Vidal*
Katherine Kelly Vidal
*Director of the United States Patent and Trademark Office*